United States Patent [19]

Hamilton et al.

[11] Patent Number: 4,673,670

[45] Date of Patent: Jun. 16, 1987

[54] N[6]-ACENAPHTHYL ADENOSINES AND ANALOGS THEREOF

[75] Inventors: Harriet W. Hamilton; William C. Patt, both of Chelsea; Bharat K. Trivedi, Canton, all of Mich.

[73] Assignee: Warner-Lambert Company, Morris Plains, N.J.

[21] Appl. No.: 857,891

[22] Filed: Apr. 30, 1986

Related U.S. Application Data

[60] Division of Ser. No. 771,591, Sep. 5, 1985, which is a continuation-in-part of Ser. No. 665,195, Oct. 26, 1984, abandoned.

[51] Int. Cl.[4] .............................................. A61K 31/70
[52] U.S. Cl. ..................................................... 514/46
[58] Field of Search ............................ 536/26; 514/46

[56] References Cited

U.S. PATENT DOCUMENTS 3,590,029  6/1971  Koch et al. .......................... 536/26

FOREIGN PATENT DOCUMENTS 1670116  11/1970  Fed. Rep. of Germany .

Primary Examiner—Ethel G. Love
Attorney, Agent, or Firm—Joan Theirstein

[57] ABSTRACT

N[6]-Acenaphthyl adenosines and analogs thereof and pharmaceutically acceptable acid addition salts having highly desirable blood pressure lowering properties, processes for their manufacture and pharmaceutical compositions and methods for using said compounds and compositions are described.

10 Claims, No Drawings

$N^6$-ACENAPHTHYL ADENOSINES AND ANALOGS THEREOF

This application is a divisional of U.S. application Ser. No. 771,591, filed Sept. 5, 1985, which is a continuation-in-part of Ser. No. 665,195, filed Oct. 26, 1984, now abandoned.

BACKGROUND OF THE INVENTION $N^6$-Naphthyl-, decalinyl-, and tetralinyl-adenosines have been described in the literature as having coronary vasodilator properties. The $N^6$-naphthyladenosines are described in German Pat. No. 1,670,116. $N^6$-[Decalinyl, tetralinyl, quinolinyl, and isoquinolinyl]methyladenosines are described in German Pat. No. 2,139,107 and a tetralinyl or tetrahydronaphthyl adenosine is also described in German Pat. No. 2,402,804. U.S. Pat. No. 4,501,735 discloses $N^6$-(1 and 2-benzocycloalkyl)adenosines. Utility in each includes increased coronary flow or advantageous circulatory properties. None of these references teaches or makes obvious the acenaphthyl adenosine and analogs of the present invention.

The present compounds use novel $N^6$-side chains on adenosine, e.g., acenaphthyl and analogs thereof, and have valuable antihypertensive properties as well as coronary vasodilator activity.

SUMMARY OF THE INVENTION

Accordingly the present invention relates to a compound of the formula

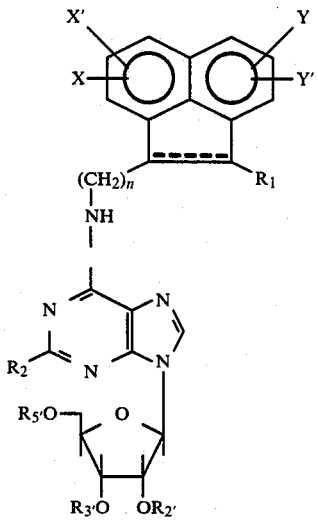

wherein:
- - - is optionally a double or single bond;
n=0-4;
X, X', Y, Y' are each independently H, OH, halogen, amino, nitro, lower alkyl, lower alkoxy or trifluoromethyl;
$R_1$=H, lower alkyl, OH or lower alkoxy;
$R_2$=H or halogen;
$R_2'$, $R_3'$, and $R_5'$=H, lower alkanoyl, benzoyl or benzoyl substituted by lower alkyl, lower alkoxy, halogen or trifluoromethyl;
$R_2'$ and $R_3'$ together may be 2', 3'-isopropylidene;
including all diastereomers and pharmaceutically acceptable acid addition salts thereof.

The present invention also relates to a pharmaceutical composition comprising a therapeutically effective amount of a compound of the above Formula I with a pharmaceutically acceptable carrier, and to a method of treating hypertension or coronary flow deficiency, such as in angina, in mammals by administering to such mammals a dosage form of a compound of the Formula I as defined above. A therapeutically effective amount is the amount effective for treating hypertension or angina in a mammal, including a human, suffering from hypertension or angina.

DETAILED DESCRIPTION OF THE EMBODIMENTS

In the compounds of the Formula I, the term "lower alkyl" is meant to include a straight or branched alkyl group having from one to six carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is O-alkyl of from one to six carbon atoms as defined above for "lower alkyl".

Lower alkanoyl is a straight or branched

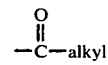

group of from one to six carbon atoms in the alkyl chain as defined above.

The compounds of Formula I are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain asymmetric carbon atoms. The invention includes the individual enantiomers or diastereomers, and mixtures thereof. The individual enantiomers or diastereomers may be prepared or isolated by methods known in the art.

A preferred embodiment of the present invention is a compound of the Formula I wherein X, X', Y, Y" are hydrogen; and n, R, $R_1$, $R_2'$, $R_3'$, and $R_5'$ are as defined above.

Another preferred embodiment is a compound of the Formula I wherein X, X', Y, Y', and $R_1$ are hydrogen, n is zero, and $R_2$, $R_2'$, $R_3'$, and $R_5'$ are as defined above.

Still another preferred embodiment is a compound of the Formula I wherein X, X', Y, Y', and $R_1$ are hydrogen, n is zero, and $R_2$ is hydrogen, and $R_2$, $R_3'$, and $R_5'$ are as defined above.

A further preferred embodiment is a compound of Formula I wherein X, X', Y, Y', $R_1$, and $R_2$ are hydrogen, n=0, and $R_2'$, $R_3'$, and $R_5'$ are hydrogen, acetyl, benzoyl or $R_2'$ and $R_3'$ when taken together are isopropylidene.

A particular embodiment includes $N^6$-(acenaphthyl)adenosine or a pharmaceutically acceptable salt thereof.

The compounds of Formula I may be conveniently synthesized by reacting a 6-halopurine riboside of Formula II with the requisite acenaphthyl amine of Formula III in an inert solvent such as alcohol, or an aprotic solvent such as dimethylformamide between about 25° to about 130° C. for from 1-48 hours. It is useful to add a base such as triethylamine, or calcium carbonate to neutralize the hydrogen halide formed as a byproduct of the reaction, but this can also be accomplished by using an extra equivalent of the aryl alkylamine. It is also convenient, although not necessary, to protect the ribofuranose hydroxyl groups as acetate or benzoate esters which can be removed with ammonium hydroxide or sodium methoxide following the synthesis of the $N^6$-substituted adenosine. The reaction is illustrated as follows:

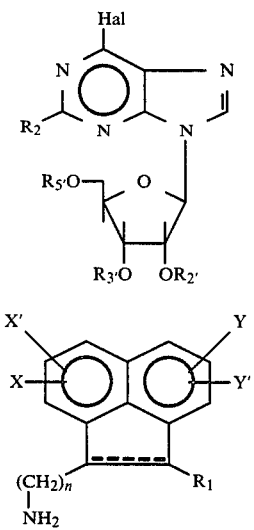

wherein Hal is halogen, preferably chlorine or bromine, and Y, Y', X, X', $R_1$, n, $R_2'$, $R_3'$ and $R_5'$ are as defined for Formula I.

The starting amine of Formula III may be prepared from a compound of the formula

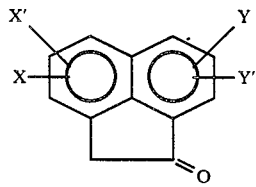

wherein X, X', Y, and Y' are as defined above by first converting the ketone to the corresponding oxime with hydroxylamine hydrochloride followed by reduction of the oxime, for example, with Raney nickel catalytic hydrogenation.

Other starting materials are either known or may be prepared by known methods.

The compounds of Formula I have been found to possess differing affinities for adenosine receptors (designated $A_1$ and $A_2$ receptors for convenience). These compounds are useful as antihypertensive agents for the treatment of high blood pressure.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150-200 g) was homogenized in 30 volumes of ice-cold 0.05M Tris-HCl buffer pH 7.7 using a Brinkman Polytron PT-10, (setting number 6 for 20 seconds) and centrifuged for ten minutes at $20,000 \times g$ (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05M Tris-HCl buffer pH 7.7 to a concentration of 20 mg/ml original wet tissue weight and used immediately.

Assay Conditions

Tissue homogenate (10 mg/ml) was incubated in 0.05M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding ($IC_{50}$) was determined by nonlinear computer curve fit. The Scatchard plot was calculated by linear regression of the line obtained by plotting the amount of radioligand bound (pmoles/gram of tissue) versus $$\left[ \frac{\text{bound radioligand}}{\text{free radioligand}} \right].$$

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[\frac{\text{bound radioligand}}{B_{max} - \text{bound radioligand}}\right].$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Ark.). Fresh brains from male Long-Evans hooded rats (Blue Spruce Farms, Altamont, N.Y.) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkman) at setting 5. The suspension was centrifuged at 50,000×g for ten minutes, the supernatant discarded, the pellet resuspended in 10 vol ice-cold Tris as above, recentrifuged, resuspended at 1 g/5 ml, and stored in plastic vials at −70° C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM $N^6$-cyclopentyladenosine (to eliminate $A_1$ receptor binding), 10 mM $MgCl_2$, 0.1 units/ml of adenosine deaminase and 1% dimethylsulfoxide. $N^6$-Cyclopentyladenosine was dissolved at 10 mM in 0.02N HCl and diluted in Tris. Stock solutions and dilutions of $N^6$-cyclopentyladenosine could be stored at −20° C. for several months. Test compounds were dissolved at 10 mM in dimethylsulfoxide on the same day as the experiment, and diluted in dimethylsulfoxide to 100× the final incubation concentration. Control incubations received an equal volume (10 μl) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 μM, the order of additions was test compound (10 μl), $N^6$-cyclopentyladenosine (100 μl), [$^3$H]NECA (100 μl), and membranes (0.79 ml). For test compounds with $IC_{50}$ values greater than 1 μM and limited water solubility, the order of additions (same volumes) was test compound, membranes, $N^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about twelve seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 μM $N^6$-cyclopentyladenosine, and specific binding was was defined as total binding minus nonspecific binding. The $IC_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the $IC_{50}$ of the drug Weighting factors were calculated under the assumption that the standard deviation was proportional to the predicted value of Y. Nonspecific binding was treated as a very large (infinite) concentration of drug in the computer analysis.

The $IC_{50}$ values (nM) for adenosine $A_1$ and $A_2$ receptor affinity for $N^6$-acenaphthyladenosine were 640 for RBA-1 and 950 for RBA-2; for $N^6$-(1-acenaphthylenylmethyl)adenosine was 92 for RBA-1 and 63 for RBA-2; and $N^6$-[(1,2-dihydro-1-acenaphthylenyl)methyl]adenosine were 6 for RBA-1 and 24 for RBA-2.

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

A Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method

Cannulation Procedure: Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over-and over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, Mass.) by means of PE100 tubing. While on test, each rat received a continuous slow infusion of heparinized saline solution (approximately 400 l or 40 units of heparin per 24 hour period) to prevent clot formation. Additional "flushes" of the cannula with heparinized saline were carried out when the aortic pulse pressure (systolic minus diastolic) was less than 25 mm Hg.

CADCS: The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main reserach computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the above procedures, compounds of Examples produced the following changes in MAP (mean arterial pressure) and heart rate.

|  | mg/kg |  | Hour |  |  |  |  |
|---|---|---|---|---|---|---|---|
|  |  |  | 1 | 3 | 5 | 7 | 9 |
| Example 1 | 10 | MAP | ↓22% | ↓17% | ↓17% | ↓15% | ↓17% |
|  |  | HR | ↑3% | ↑13% | ↑19% | ↑17% | ↑9% |

-continued

|  | mg/kg |  | Hour |  |  |  |  |
|---|---|---|---|---|---|---|---|
|  |  |  | 1 | 3 | 5 | 7 | 9 |
|  | 30 | MAP | ↓30% | ↓20% | ↓26% | ↓29% | ↓29% |
|  |  | HR | ↑6% | ↑15% | ↑25% | ↑24% | ↑19% |
| Example 2 | 10 | MAP | ↓48% | ↓30% | ↓26% | ↓20% | ↓21% |
|  |  | HR | 0% | ↑10% | ↑12% | ↑19% | ↑14% |
| Example 3 | 10 | MAP | ↓27% | ↓15% | ↓14% | ↓17% | ↓13% |
|  |  | HR | ↑4% | ↑19% | ↑20% | ↑11% | ↑13% |

Coronary Blood Flow Evaluation

The usefulness of the compounds of the present invention as agents effective to treat angina, is shown by their effectiveness in standard pharmacological test procedures, for example, in causing significant increase in coronary blood flow in rats. This test procedure is described in the following paragraphs.

Method

Male rats (400–600 gms) are pretreated with Na heparin 2000 units and anesthetized with Na pentobarbital (50 mg/kg) administered intraperitoneally. Once anesthetized, the rat heart is rapidly excised, the ascending aorta fitted to the aortic perfusion cannula, and secured with a ligature. The coronary arteries are perfused initially at a rate of about 15 ml/min for two to three minutes, after which they are perfused at constant pressure of 70 mm Hg and temperature of 37° C. The electrocardiogram (ECG) is recorded using two platinum electrodes positioned at the base and apex of the left ventricle. A second heart is excised, cannulated, and perfused by the same method outlined above. Both hearts are tested in parallel. The standard physiological salt solution (PSS) is a modified Krebs-Hanseleit bicarbonate buffer of the following composition in mM concentration: NaCl, 127; $NaHCO_3$, 25; dextrose, 5.5; Na Pyruvate, 2.0; KCl, 4.7; $MgSO_4$, 1.1; $KH_2PO_4$, 1.2; $CaCl_2.2H_2O$, 2.5; $CaNa_2EDTA$, 0.05.

A 30-minute stabilization period is observed before starting the test protocol.

Microprocessor Controlled Coronary Perfusion and Drug Delivery System

The microprocessor control system is a servo mechanism which permits coronary perfusion pressure (CPP) and drug concentration to be maintained constant independent of changes in coronary flow. The level at which CPP and drug concentration are maintained can be changed by commands communicated through the microprocessor keyboard. Dose-response curves are carried out by perfusing concentrated drug solution (DC) at rates proportional to total coronary flow ($CF_T$). Drug concentrations are increased by proportionate increases in the rate of DC infusion over $CF_T$ via the microprocessor keyboard. The proportional flow rates for DC:$CF_T$ is about 0.0002:1 at the low end and 0.02:1 at the high end of the dose-response curve. Dose-response curves encompassing at least two log doses are carried out by preparing two DCs with a concentration difference of 1:100. Following the first dose range of two log doses, the DC are switched, proportional pumping rate adjusted, and the dose-response curve continued for another two log doses. The standard dose-response curve is carried out in one-half log dose increments starting at a subthreshold dose and ending at a dose which produces near maximal response in activity. Standard reference compounds are tested over the range of $10^{-9}$ to $10^{-6}$M.

Measurements

Measurements are for heart rates (HR) and coronary flow (CF). Units are: HR, beats/minute (bpm) and CF, milliliters/minute (ml/min). HR is calculated from the ECG strip chart recording and CF is calculated by recording analog outputs from pumps 1 and 2. Outputs from pump #1=$CF_T$ and the output from pump #2=CF for heart B ($CF_B$). CF for heart A ($CF_A$) is calculated ($CF_T - CF_B = CF_A$).

Using the above technique, the effects of the compound of Examples 1, 2 and 3 are as follows indicating the compound of Example 3 is preferred to increase coronary blood flow.

| Dose (Molar) | Example 1 | | Example 2 | | Example 3 | |
|---|---|---|---|---|---|---|
| | % ↑ CF | % ↓ HR | % ↑ CF | % ↓ HR | % ↑ CF | % ↓ HR |
| $1 \times 10^{-9}$ | NT* | NT | 2 | −1 | NT | NT |
| $3 \times 10^{-9}$ | NT | NT | 7 | −1 | NT | NT |
| $1 \times 10^{-8}$ | 0 | 1 | 37 | 1 | 41 | 2 |
| $3 \times 10^{-8}$ | 7 | 0 | 48 | 4 | 49 | 8 |
| $1 \times 10^{-7}$ | 27 | 2 | NT | NT | 58 | 36 |
| $3 \times 10^{-7}$ | 40 | 2 | 60 | 25 | 67 | 44 |
| $1 \times 10^{-6}$ | 44 | 5 | 62 | 30 | 62 | 65 |
| $3 \times 10^{-6}$ | 49 | 8 | NT | NT | 67 | 68 |

*NT means not tested

The present invention further includes a method for treating hypertension or angina in mammals suffering therefrom comprising administering to such mammals either orally or parenterally a corresponding pharmaceutical composition containing a compound of the Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Example further illustrates the invention.

EXAMPLE 1

$N^6$-Acenaphthyladenosine

6-Chloropurine riboside (2.8 g, 10 mmol) was added, at once, to a solution of the 1-aminoacenaphthene.HCl (2.1 g, 10 mmol) and triethylamine (2.5 g, 25 mmol) in ethanol (150 mL). This solution was stirred at reflux overnight. The solution was cooled to room temperature, then to 8° C. to precipitate. The solid collected by filtration was dried in vacuo at 65° C. overnight: yield 1.8 g (43%); mp 146.5°–150° C. Anal. ($C_{22}H_{21}N_5O_4$), calc: C=63.00, H=5.05, N=16.70; found: C=62.95, H=5.12, N=16.70.

The synthesis of the starting amine from the known ketone follows:

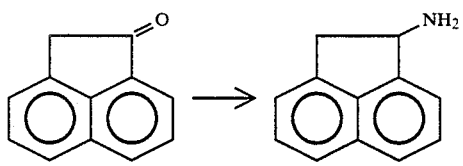

A solution of hydroxylamine.HCl (5.7 g, 82 mmol) and sodium acetate (6.7 g, 82 mmol) in water (50 mL) was added, in a steady stream, to a solution of the ketone[1] (4.6 g, 27.5 mmol) in ethanol (100 mL). The new solution was stirred at reflux for four hours then cooled to room temperature and allowed to stand overnight. The solution was evaporated to dryness in vacuo and the residue stirred into water (200 mL). The precipitate was collected by filtration and dried in vacuo at 45° C. for seven hours: yield 4.8 g (96%); mp 174°–178°; $^1H$. Anal. ($C_{12}H_9NO.0.15H_2O$), calc: C=77.53, H=4.96, N=7.53; found: C=77.60, H=5.32, N=7.56.

[1]H: E[13],164: Elsevier's Encyclopedia

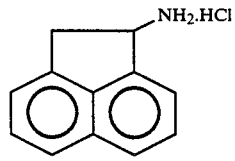

The oxime (4.88 g, 26 mmol) was dissolved in ammonia saturated (R.T.) methanol (100 mL) and Raney nickel (1.5 g) added. The solution was pressurized with $H_2$ at room temperature for 68.5 minutes then warmed to 40° C. for an additional 1188.5 minutes. The mixture was cooled to room temperature and the pressure released. The mixture was filtered free of catalyst and catalyst washed with THF (100 mL). The combined organic layers were evaporated in vacuo and the residue added to isopropanol/HCl (saturated R.T.). The solution was cooled to 8° C. to precipitate. The solid was collected by filtration and dried in vacuo at 45° C. for five hours: yield 3.9 g (74%); mp >290. Anal. ($C_{12}H_{11}N.HCl$), calc: C=70.07, H=5.88, N=6.81, $Cl^-$=17.23; found: C=71.59, H=5.95, N=6.20, $Cl^-$=17.26. $H^1$ NMR (D6-DMSO, 200 mHz): $\delta$3.33 (d of d, J=18 Hz 2 Hz, 1H), $\delta$3.82 (d of d, J=8 Hz, 18 Hz, 1H), $\delta$5.22 (n, 1H), $\delta$7.38–7.89 (n, 6H), $\delta$8.76 (s, 3H).

EXAMPLE 2

$N^6$-(1-acenaphthylenylmethyl)adenosine

Six chloropurine riboside (1.15 g, 4 mmol), triethyl amine (1.0 g, 10 mmol) and the N-[(1-acenaphthylenyl)-methyl]amine, A, as prepared in the following Example A (1.0 g, 4.6 mmol) were stirred at reflux in ethanol (100 ml) overnight. The solution was cooled to room temperature and filtered free of precipitate. The solid washed with ethanol (50 ml) and dried at 45° C., in vacuo, overnight to give 1.55 g (91%) of a white solid, of N-(1-acenaphthylenylmethyl)adenosine having a mp of 148.5°–150° C. Anal. ($C_{23}H_{21}N_5O_4.0.25EtOH$), calc: C=63.72, H=5.12, N=15.81; found: C=63.49, H=4.99, N=15.78.

EXAMPLE 3

$N^6$-[(1,2-Dihydro-1-acenaphthylenyl)methyl]adenosine

Six chloropurine riboside (1.7 g, 6 mmol), triethyl amine (1.5 g, 15 mmol) and the N-[(1,2-dihydro-1-acenaphthylenyl)methyl]amine, B, as prepared in the following Example B (1.4 g, 6.4 mmol) were stirred at reflux in ethanol (100 ml) overnight. The solution was cooled to room temperature and filtered free of solid. The solution was washed with ethanol (50 ml) and dried at 65° C. in vacuo for four hours, to give 2.2 g (85%) of a white solid, mp 173°–175° C. Anal. ($C_{23}H_{23}N_5O_4$); calc: C=63.73, H=5.35, N=16.16; found: C=63.55, H=5.49, N=16.00.

EXAMPLE A

N-[(1-Acenaphthylenyl)methyl]amine

Acenaphthanone (8.4 g, 50 mmol) and zinc (II) iodide (~15 mg) were treated with trimethylsilylcyanide (5.5 g, 55 mmol) and stirred in absence of solvent at room temperature, overnight. The reaction mixture was slurried in dry THF (150 ml) and added, dropwise, to a slurry of lithium aluminum hydride (LAH) (2.1 g, 55 mmol) in THF (150 ml). The new solution was slowly (two hours) warmed to reflux and stirred for four hours. The reaction was cooled to room temperature and carefully quenched with watr (100 ml). The slurry treated with 1N NaOH (50 ml) and filtered free of solids. The solids were washed with THF (200 ml) and the combined filtrates evaporated free of THF. The aqueous solution was extracted with ether (3×200 ml) and the organic solution washed successively with 1N NaOH (100 ml), water (100 ml), and saturated brine solution (100 ml). The organic solution was dried over magnesium sulfate and the solvents evaporated in vacuo. The residue was stirred into HCl saturated ethanol (150 ml) and warmed to 50° C. for 2.5 hours. The ethanol was evaporated in vacuo to ~50 ml and cooled to 8° C. The precipitated solid was collected by filtration and dried in vacuo at 65° C. for six hours, to give 3,2 g (30%) of the white hydrochloride salt, mp d245° C. Anal. ($C_{13}H_{11}N.HCl$); calc: C=71.72, H=5.56; N=6.44, $Cl\theta$=16.28; found: C=71.69, H=5.67, N=6.35, $Cl\theta$=16.00

EXAMPLE B

N-[(1,2-Dihydro-1-acenaphthylenyl)methyl]amine

The N-[(1-acenaphthylenyl)methyl]amine hydrochloride, A as prepared in Example A above (1.8 g, 8.3 mmol) was dissolved in methanol (100 ml) and 5% Pd/C (0.2 g) added. The mixture was stirred at room temperature, under 51 psi of hydrogen, for 2.5 hours (hydrogen uptake: AP=6.8 psi, calculated 7.1). The catalyst was removed by filtration and the solvent evaporated in vacuo. The residue was treated with ether (150 ml) and filtered to collect precipitate. The solid was dried at 45° C., in vacuo, overnight, to give 1.5 g (83%) of a white N-[(1,2-dihydro-1-acenaphthylenyl)methyl]amine hydrochloride salt, mp >250° C. Anal ($C_{13}H_{13}N \cdot HCl \cdot 0.15H_2O$), calc: C=71.20, H=6.48, N=6.30, Cl=15.54; found: C=70.14, H=6.51; N=6.42; Cl=16.11.

We claim:

1. A method of treating angina in a mammal suffering therefrom, which comprises administering to such mammal an anti-angina effective amount of a compound of the formula

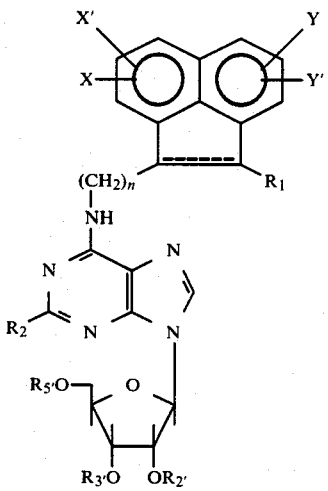

wherein:
- - - is optionally a double or single bond;
n=zero to four;
X, X', Y, Y' are each independently H, OH, halogen, amino, nitro, lower alkyl, trifluoromethyl or lower alkoxy;
$R_1$ is H, alkyl, OH or lower alkoxy;
$R_2$ is H or halogen;
$R_2'$, $R_3'$, and $R_5'$ are each independently hydrogen, alkanoyl, benzoyl, benzoyl substituted by lower alkyl, lower alkoxy, halogen or trifluoromethyl; or
$R_2'$ and $R_3'$ together may be 2', 3'-isopropylidene, or a pharmaceutically acceptable acid addition salt thereof.

2. A method according to claim 1, wherein X, X', Y, and Y' are hydrogen.

3. A method according to claim 2, wherein $R_1$ is hydrogen and n is zero.

4. A method according to claim 2 wherein $R_1$ is hydrogen and n is one.

5. A method according to claim 3, wherein $R_2$ is hydrogen.

6. A method according to claim 5, wherein $R_2'$, $R_3'$, and $R_5'$ are each independently hydrogen, acetyl or benzoyl, or $R_2'$ and $R_3'$ when taken together are isopropylidene.

7. A method according to claim 6 and being $N^6$-(acenaphthyl)adenosine.

8. A method according to claim 4 wherein $R_2'$, $R_3'$, and $R_5'$ are each independently hydrogen, acetyl or benzoyl, or $R_2'$ and $R_3'$ when taken together are isopropylidene.

9. A method according to claim 8 and being $N^6$-(1-acenaphthylenylmethyl)adenosine.

10. A method according to claim 9 and being $N^6$-[(1,2-dihydro-1-acenaphthylenyl)methyl]adenosine.

* * * * *

UNITED STATES PATENT AND TRADEMARK OFFICE
CERTIFICATE OF CORRECTION

PATENT NO. : 4,673,670

DATED : June 16, 1987

INVENTOR(S) : Harriet W. Hamilton, William C. Patt, Bharat K. Trivedi

It is certified that error appears in the above—identified patent and that said Letters Patent is hereby corrected as shown below:

In Column 14, line 23, change "- - -" to -- ===== --

Signed and Sealed this

Nineteenth Day of January, 1988

Attest:

DONALD J. QUIGG

Attesting Officer

Commissioner of Patents and Trademarks